(12) United States Patent
Greenfield

(10) Patent No.: US 8,113,828 B1
(45) Date of Patent: Feb. 14, 2012

(54) ORTHODONTIC BRACKET

(76) Inventor: Raphael L. Greenfield, Delray Beach, FL (US)

( * ) Notice: Subject to any disclaimer, the term of this patent is extended or adjusted under 35 U.S.C. 154(b) by 0 days.

(21) Appl. No.: 12/807,859

(22) Filed: Sep. 14, 2010

(51) Int. Cl.
*A61C 7/14* (2006.01)
(52) U.S. Cl. .......................................... 433/16; 433/10
(58) Field of Classification Search .................. 433/8–17
See application file for complete search history.

(56) References Cited

U.S. PATENT DOCUMENTS

| | | | |
|---|---|---|---|
| 2,368,851 A | 2/1945 | Laskin | |
| 2,379,011 A | 6/1945 | Laskin | |
| 3,423,833 A | 1/1969 | Pearlman | |
| 3,721,005 A | 3/1973 | Cohen | |
| 4,139,945 A | 2/1979 | DiGiulio | |
| 4,209,906 A * | 7/1980 | Fujita | 433/11 |
| 4,243,387 A | 1/1981 | Prins | |
| 4,353,692 A | 10/1982 | Karrakussoglu | |
| 4,597,739 A | 7/1986 | Rosenberg | |
| 4,867,678 A | 9/1989 | Parker | |
| 5,302,121 A | 4/1994 | Gagin | |
| 5,954,502 A | 9/1999 | Tuenge et al. | |
| 7,306,458 B1 * | 12/2007 | Lu et al. | 433/16 |
| 7,431,586 B1 * | 10/2008 | Silverman | 433/9 |
| 2008/0293005 A1 * | 11/2008 | Rahlis et al. | 433/16 |

* cited by examiner

*Primary Examiner* — Todd Manahan
*Assistant Examiner* — Michael R Ballinger
(74) *Attorney, Agent, or Firm* — Chernoff, Vilhauer, McClung & Stenzel, LLP

(57) ABSTRACT

An orthodontic bracket mountable on a tooth for use in retraction mechanics to facilitate movement of teeth along an arch, which includes an archwire receiving member rotatably mounted on a base and structured to freely rotate when tipping a tooth during sliding of the bracket along an archwire thereby minimizing friction between the archwire and bracket to significantly decrease the required retraction force, and treatment time, thereby minimizing the possibility of root resorption and maintaining the integrity of the root and surrounding bone. A locking pin for locking the member against rotation is employed when uprighting the tooth from a tipped position.

19 Claims, 5 Drawing Sheets

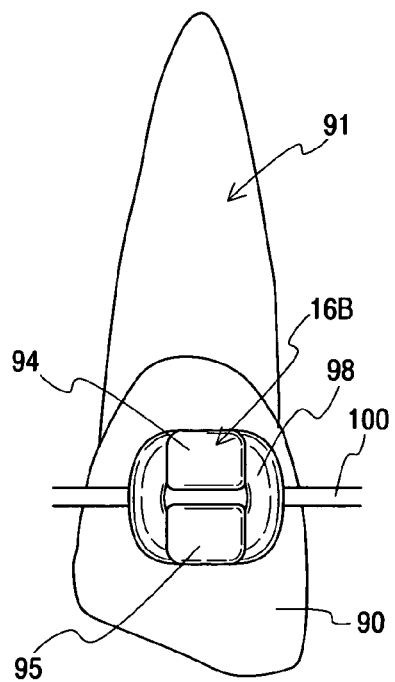
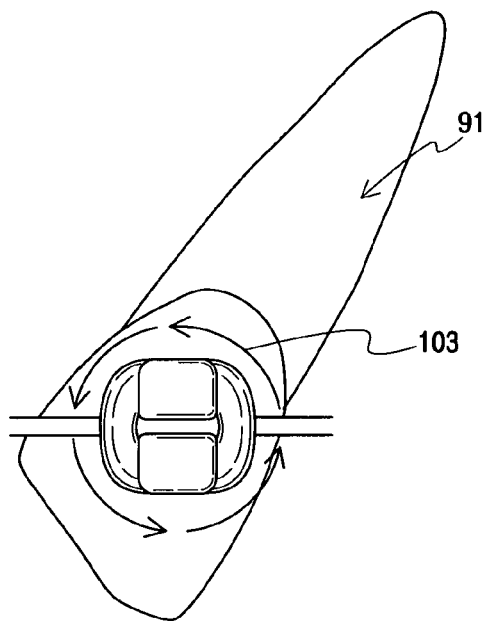
*Fig. 8a*  *Fig. 8b*
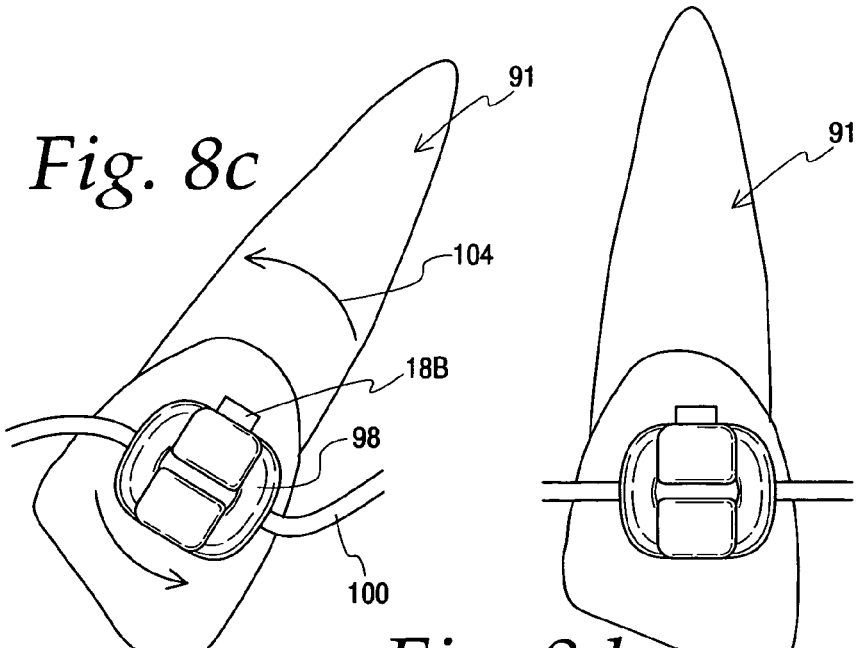
*Fig. 8c*
*Fig. 8d*

ORTHODONTIC BRACKET

TECHNICAL FIELD

This invention relates to a new and improved orthodontic bracket appliance for use in edgewise or straight-wire techniques to facilitate tipping movement of a tooth and sliding of the bracket along an archwire, including structure to minimize frictional resistance, thereby reducing the time of completing the movement to the desired location along the arch, and enhancing the health and comfort of the patient.

BACKGROUND OF THE INVENTION

With regard to employment of retraction mechanics, it is well known that free tipping tooth movement is arguably the most efficient type of tooth movement in orthodontics, inasmuch as with such tooth movement the teeth move faster with the least amount of force. During retraction mechanics there may be retraction of incisors, cuspids or bicuspids, and where the teeth move faster with lighter forces applied during the treatment. It is also known that lighter forces significantly reduce the possibility of root resorption of orthodontically induced tooth movements. Further, lighter forces enhance the success of differential force systems, inasmuch as during retraction mechanics, forces are applied between larger posterior anchor teeth, such as molars or premolars, and anterior teeth, such as incisors, bicuspids or bicuspids. With lighter forces the positions of these anchor teeth will essentially be undisturbed during retraction of incisors, cuspids or bicuspids.

Heretofore, it has been well known to employ retraction mechanics for moving teeth in the edgewise and straight-wire techniques with brackets having rotatable archwire engaging members that may allow to an extent tipping and uprighting, such as disclosed in U.S. Pat. Nos. 4,867,678 and 5,302,121. However, with respect to these bracket appliances, the increased frictional resistance during retraction mechanics extends the time needed to complete the retraction goals, and the time of patient treatment requires heavier forces which may cause root resorption, as well as adversely affecting the comfort of the patient.

SUMMARY OF THE INVENTION

The bracket of the present invention includes a unique feature to minimize friction between a rotating archwire receiving member and a base mountable on a tooth so as to reduce the friction between the archwire and the archwire receiving member of the bracket. Accordingly, the time of retraction movement of a tooth on which the bracket is mounted to a desired position is significantly shortened. Root resorption is minimized due to the application of light forces, thereby maintaining the integrity of the root and surrounding bone. Accordingly, comfort to the patient is greatly enhanced. This is accomplished in that the bracket includes a base mountable on a tooth and an archwire receiving member rotatably mounted on the base wherein engageable surfaces between the archwire receiving member and the base include means for reducing friction during rotation of the archwire receiving member on the base member. The archwire receiving member and the base member include bars with protrusions between the sliding surfaces of the bars and/or any retention part of a stud or shaft secured to the base on which the archwire receiving member rotates. The bars with protrusions may have different shapes, such as rectangular, square or semicircular. Additionally, these bars serve to coact with a unique locking pin to lock the archwire receiving member against rotation on the base when the desired movement has been obtained so that forces can be applied to the bracket to direct it to its desired erect position. The archwire receiving member is rotated so that it is aligned with respect to the tooth and a locking pin can be inserted to lock the archwire receiving member to the base. In this position, the predetermined prescription of the bracket to move the tooth to its ideal position will be achieved.

It will be appreciated that the appliance of the invention may be designed with any of the well known prescriptions utilized in the orthodontic field to obtain the desired final positioning of the teeth on which the appliance is mounted. It may also be made of various materials, such as ceramic, zirconia, plastic or acrylic. Accordingly, in the final stages of treatment, a locking pin is inserted to lock the archwire receiving member to the base. The archwire must first be removed from the archwire slot before rotating and locking the archwire receiving member to the base. Following insertion of the locking pin, the archwire receiving member cannot rotate relative to the base. Thereafter, the archwire is flexed as needed and reinserted into the slot, and ligated to the archwire receiving member after which the tooth will be uprighted into its ideal position.

BRIEF DESCRIPTION OF THE DRAWINGS

FIGS. 8*a*, 8*b*, 8*c* and 8*d* are front elevational views of a tooth diagrammatically illustrating the operation of the bracket of the invention through the tipping and uprighting movements, and on which a modified bracket of the invention is mounted with an archwire retained in the archwire slot as shown in FIG. 8*a*, and the steps of tipping of the tooth as shown in FIG. 8*b*, the use of the locking pin where the archwire has been flexed and reinserted into the bracket as shown in FIG. 8*c*, and wherein the final position of the tooth is moved by the forces of the archwire and/or other uprighting devices to upright the tooth as shown in FIG. 8*d*;

DETAILED DESCRIPTION OF THE INVENTION

Figure 1:
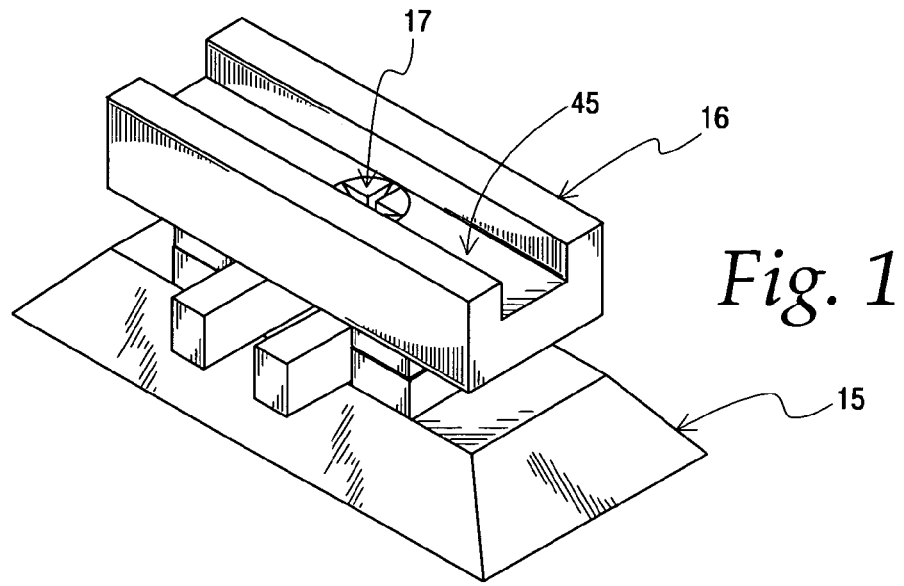
FIG. 1 is a perspective view of an orthodontic bracket according to the invention wherein the archwire receiving member is locked to the base with the locking pin.
Figure 2:
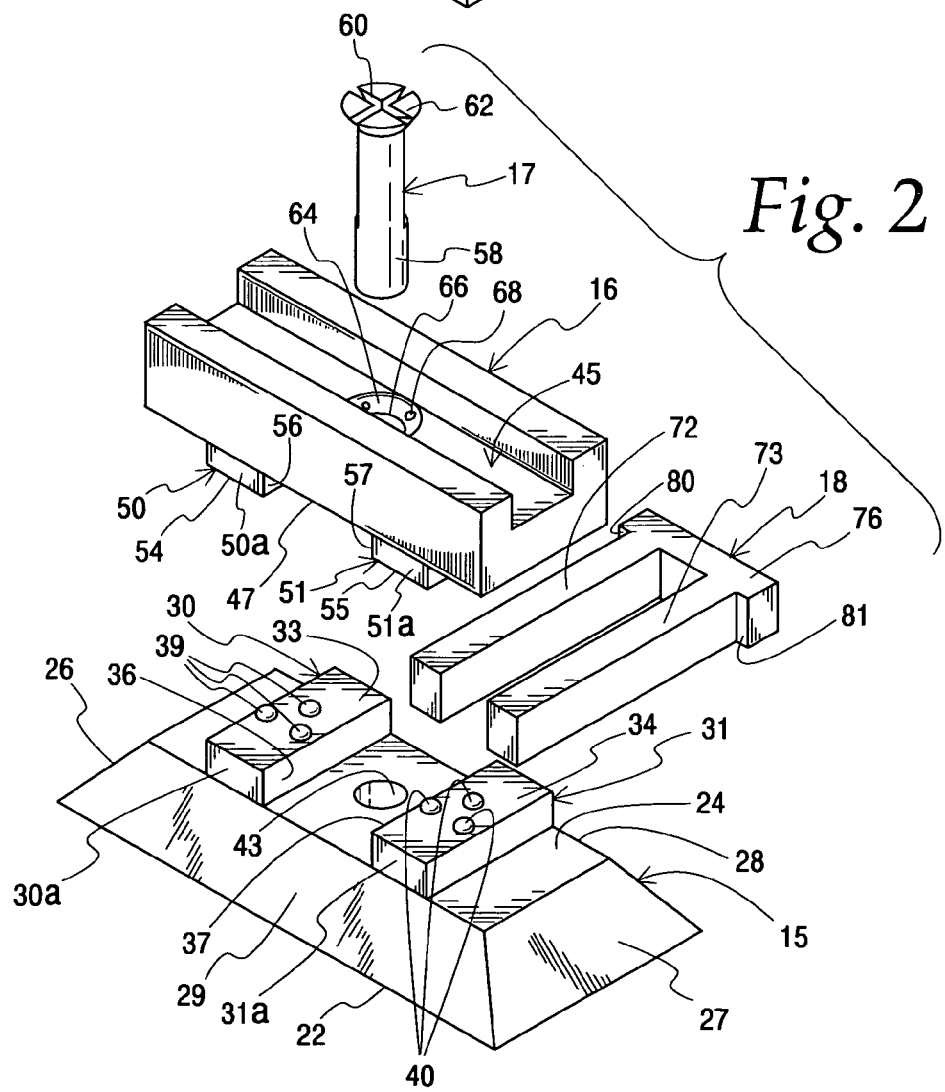
FIG. 2 is an exploded perspective view of the bracket of FIG. 1 showing the base, the archwire, receiving member, the stud or shaft on which the archwire receiving member is rotatably mounted and the locking pin employed to lock the archwire receiving member to the base in the final stages of treatment.
Figure 3:
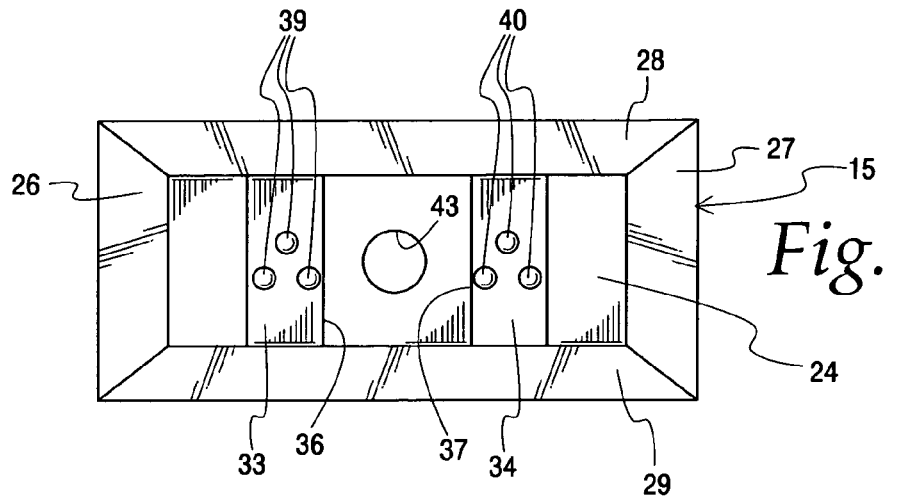
FIG. 3 is a front elevational view of the base of the bracket.

Referring now to the drawings, and particularly to the embodiment of FIGS. 1-7, the orthodontic bracket of the invention includes generally a base 15 and an archwire receiving member 16 rotatable on the base. A stud, generally indicated by the numeral 17, coacts with the archwire receiving member 16 and is suitably anchored in the base 15 for rotatably mounting the archwire receiving member 16 on the base. It will be appreciated that the base on the archwire receiving member may be of various shapes and the embodiment of FIGS. 1-7 is primarily illustrative of the invention and the parts of the bracket that produce the rotational mounting of the archwire receiving member on the base and the ability to employ a locking pin, generally indicated by the numeral 18, for locking the archwire receiving member to the base during the final stage of treatment. The coacting bearing or sliding surfaces, resulting from rotation of the archwire receiving member on the base, include means to minimize friction between the surfaces so that the archwire receiving member can freely rotate on the base. It will be appreciated that the bracket may be made of any suitable metal or ceramic.

The base 15 in this embodiment includes a lingual or back face 22 that may be suitably contoured if desired to be bonded to a tooth for mounting the bracket on a tooth. The base further includes a front or buccolabial face 24, sloping mesial and distal faces 26 and 27, and sloping gingival and occlusal faces 28 and 29. It will be understood that the general shape of the base is rectangular although it may take any suitable geometric form. A pair of mesiodistally spaced bearing bars 30 and 31 are integral with and located on the front face 24 of the base against which opposing bearing bars on the archwire receiving member engage. These bars, as will be more clearly hereinafter understood, are substantially parallel to each other, and not only serve to coact with opposing bars on the archwire receiving member to position the archwire receiving member in spaced relation to the base, but also to coact with the locking pin 18 for locking the archwire receiving member 16 to the base 15. The bars 30 and 31 include top surfaces 33 and 34 that are generally parallel to the front face 24 of the base vertically extending locking pin engaging faces 36 and 37, and occlusal ends 30a and 31a. On the top surfaces 33 and 34 of the bars a plurality of dome-shaped protrusions or buttons 39 and 40 are provided for bearing engagement with the opposing flat surfaces of the bars on the archwire receiving member 16, defining a bearing for said stub or shaft 17, as will be further explained. A blind hole 43 is centrally located in the base between the bars 30 and 31 for receiving the stud or shaft 17, as will be further explained.

The archwire receiving member 16 is rectangular in shape, similar to the base 15, although it may take any suitable shape, and includes an outwardly opening rectangular archwire receiving slot 45 defined on the buccolabial side of the member. For purposes of symmetry in the illustrated embodiment of FIGS. 1-7, the archwire receiving member is rectangular in shape as is the base although as mentioned it may take any desirable shape. Additionally, the archwire receiving member includes a back or labial face 47 on which are mesiodistally spaced apart bars 50 and 51 having flat labial bearing faces 54 and 55 respectively, and vertically extending locking faces 56 and 57 which coact with the locking pin.

As above mentioned, the labial faces 54 and 55 are flat surfaces that contact or engage against the protrusions 39 and 40 on the opposing bars 33 and 34 of the base. The inclusion of the protrusions which engage the flat faces of the archwire receiving member bars substantially reduce the frictional sliding engagement between the bars of the base and archwire receiving member so as to minimize the friction and facilitate the ease of rotation of the archwire receiving member on the base. It will be appreciated that while the protrusions are shown on the bearing bars of the base, they may be provided on the bearing bars of the archwire receiving member. In that event, the engaging faces of the base bars will be flat.

Figure 7:
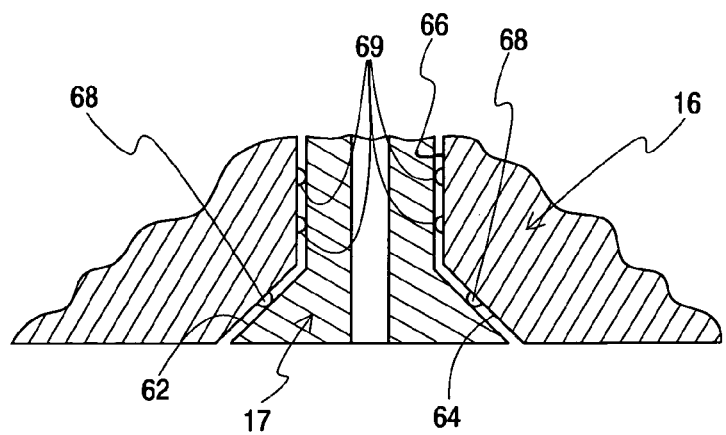
FIG. 7 is a greatly enlarged cross-sectional view of a part of the archwire receiving member and showing the shaft on which the archwire receiving member is mounted and which illustrates further the protrusions on the rotatable archwire receiving member engaging a part of the stud.

The stud or shaft 17 on which the archwire receiving member rotates is suitably anchored in the blind hole 43 when the archwire receiving member is assembled with the base. The stud 17 includes a substantially cylindrical end 58 sized relative to the hole 43 of the base so that it can be press-fitted into the hole when locking the archwire receiving member to the base. Further, it will be appreciated that the stud 17 may be integrally formed with the base, such as if made by investment casting. Where the shaft is first secured to the base, the archwire receiving member may be thereafter mounted onto the stud by virtue of a crisscross cut 60 at the outer end of the stud allowing the head of the stud to collapse as the archwire receiving member is mounted thereon and to resiliently expand once the archwire receiving member is positioned to allow the engagement between bars 33, 34 of the base and 50, 51 of the archwire receiving member. If the shaft is assembled after placement of the archwire receiving member on the base, it need not include the cross-cut. The outer end of the shaft includes a conical bearing surface 62 on the head of the shaft that coacts with a conical bearing surface 64 at the outer end of a bearing 66 on the archwire receiving member that engages the main body of the shaft 17. To further reduce the friction between the stud 17 and the archwire receiving member 16, protrusions or buttons 68 are provided on the conical surface 64 of the member 16, and which bearingly engage the conical surface 62 of the shaft 17, as seen in FIG. 7.

Figure 4:
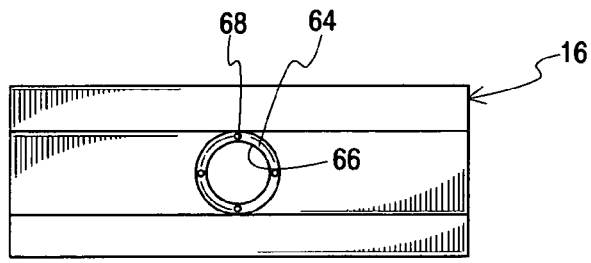
FIG. 4 is a front elevational view of the archwire receiving member of the bracket.

While any number of friction reducing protrusions may be provided on the member 16, as seen in FIG. 4, the protrusions or buttons 68 are generally equally spaced around the conical surface 64 of the bearing 66. While the protrusions are shown on the member 16, they could be only provided on the conical surface 62 of the head instead of the conical surface 64 of the member 16. In that event, the conical surface 64 would not include protrusions. Similarly, while three protrusions are provided on the outer surfaces 33 and 34 of the base bars 30 and 31, it will be appreciated that any number may be provided. The three protrusions on the bars produce a three-point contact between the bars of the base and the bars of the archwire receiving member. With respect to the stud 17 engaging the bearing of the archwire receiving member, a four-point contact is provided between the conical surface 64 and the conical surface 62. Additionally, as shown in FIG. 7, protrusions 69 may be provided on the bearing 66 for engaging the main part of the shaft or stud 17 to further reduce friction between the stud and bearing. As mentioned, any suitable number of protrusions may be provided on one of the bearing surfaces of the stud/bearing or the bars.

During the tipping of the tooth and the sliding movement of the tooth and bracket along the archwire, the archwire receiving member freely rotates on the base so that the bracket can easily slide along the archwire to the predetermined position in which the tooth may then be uprighted. It will be appreciated that suitable force modules, such as springs or elastics, will be employed to cause movement of the tooth and bracket along the archwire. Once the tooth is in the desired position and it is necessary to upright the tooth, the archwire receiving member is locked to the base so that the archwire can then apply upright forces, as will be more clearly explained below. The locking pin 18 is inserted into the bracket between the archwire receiving member and the base to engage the bearing bars of both the archwire receiving member and the base when they are aligned with each other.

Figure 5:
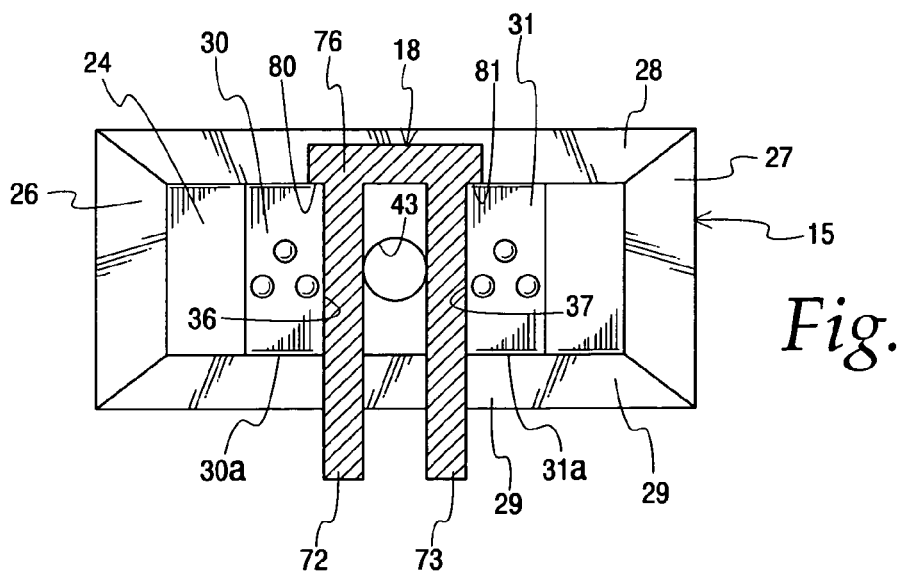
FIG. 5 is a front elevational view of the base of the bracket and a cross-sectional view taken through the locking pin as positioned relative to the base.
Figure 6:
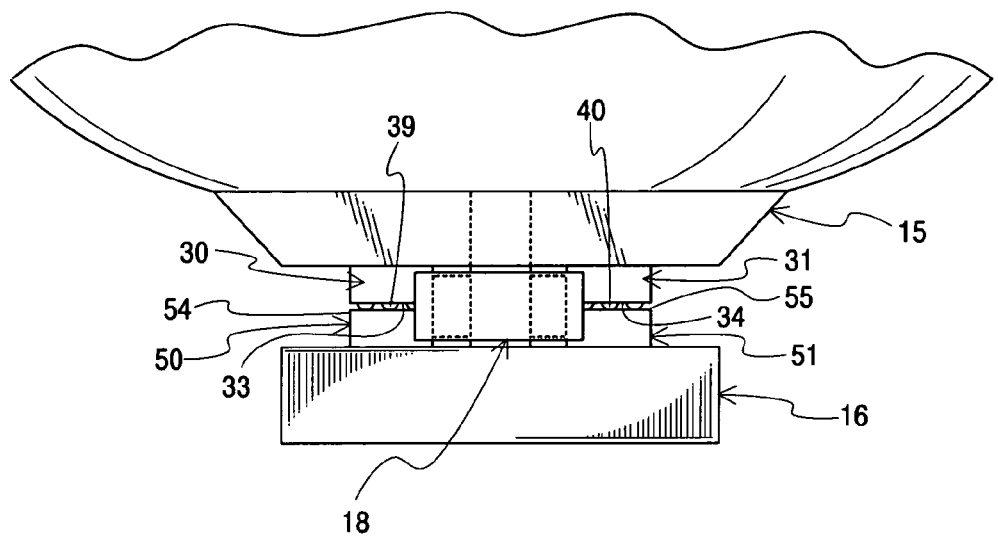
FIG. 6 is a top plan view of the bracket of FIG. 1 mounted on a tooth and showing the locking pin in position to lock the archwire receiving member to the base and showing the protrusions on the bars of the base which engage the bars of the archwire receiving member.

The locking pin 18 is generally U-shaped and includes generally parallel spaced apart legs 72 and 73 interconnected by a substantially perpendicular top bar 76. The legs 72 and 73 are generally rectangular in cross section as is the top bar 76. The locking pin 18 is sized for easy insertion into the bracket once the bearing bars 33 and 34 on the base and bearing bars 50 and 51 on the receiving member are aligned. Shoulders 80 and 81 of the locking pin are provided at the upper end of the locking pin at the ends of the top bar 76 which engage, when the pin is inserted, the upper inside corners of the base bearing bars 30 and 31 and the archwire receiving member bars 50 and 51, as generally shown in FIGS. 5 and 6. Thus, the locking pin 18 is seated in the appliance once the shoulders engage the upper corners of the bearing bars, and the free ends of the legs extend beyond the occlusal ends 30a and 31a of the base bars 30 and 31 and the occlusal ends 50a and 51a of the member bars 50 and 51.

The legs 72 and 73 are sized for easy insertion into the bracket and for engaging the vertically extending locking pin engaging surfaces 36 and 37 of the base and 56 and 57 of the archwire receiving member 16, as particularly seen in FIGS. 5 and 6. With respect to the locking pin shown in FIGS. 1, 2, 5 and 6, it may be made of soft brass so that once it is inserted as shown in FIG. 5, one or both of the free ends of the legs 72 and 73 extending over the occlusal ends 30a and 31a of the base bars 30 and 31, and the occlusal ends 50a and 51a of the members 50 and 51 bars at the occlusal surface 29 of the base may be bent over to prevent withdrawal of the pin from the bracket. During any part of the treatment, the ends of the legs may easily be cut off by a suitable instrument for removal of the pin if necessary. A new pin may be used thereafter if it is desired to continue locking the archwire receiving member to the base. It should also be appreciated the locking pin could be of any other suitable metal, such as titanium or stainless steel, or even of a suitable plastic such as a urethane which could withstand the forces encountered during treatment.

Figures 9, 10:
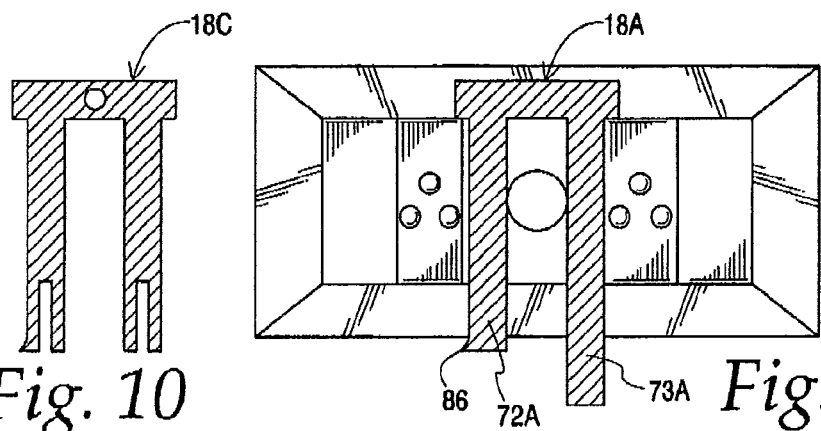
FIG. 9 is a view similar to FIG. 5 but showing a modified locking pin which is self-locking in the bracket once inserted into the bracket to lock the base and the archwire receiving member together.
FIG. 10 is a front elevational view of a self-ligating bracket wherein the archwire receiving member rotatable on the base includes a rotatable gate for opening and closing the archwire slot.

A modified locking pin 18A is shown in FIG. 9 and differs from locking pin 18 in that it includes a detent or retention member 86 on at least one of the legs 72A or 73A. This locking pin would be made of a resilient spring-back metal such as stainless steel, beta titanium, or the like, and sized wherein the leg with the locking retention member 86 would be first urged toward the opposite leg during insertion and after insertion would spring back so that the retention element would engage the occlusal ends of the bearing bars, and prevent removal of the pin except upon the application of a suitable force or the bending of the detent leg to clear the occlusal ends of the bars. The location of the detent on the leg may be other than shown, such as to latch into locking position at about the same time the shoulders 80 and 81 of the pin engage the bars 30 and 31. It will be appreciated that a detent may be provided on either or both legs if so desired.

A further modified locking pin 18C is shown in FIG. 10, which differs from the locking pins 18 and 18A in that a hole is provided in the top bar for engagement by a conventional scaler or similar dental instrument when removing the pin from the bracket. Further, both legs are slotted such that they may be squeezed together permanently to a narrower dimension to facilitate removal of the pin from the bracket. As in the pin 18A, a detent is provided on one leg for locking the pin in place on the bracket.

With respect to the embodiment of FIGS. 1-7, once the archwire receiving member 16 and stud 17 are properly mounted on the base 15, the head of the stud or shaft 17 will be substantially flush with the bottom of the archwire slot. Accordingly, the head of the stud or shaft 17 will not interfere with the sliding movement of the archwire in the archwire receiving member of the bracket. Moreover, it will be appreciated that in order to retain an archwire in the archwire receiving slot 45, suitable ligatures or ties, such as a wire ligature or tie, may be provided to overlie the archwire and the archwire receiving member and tied to hold it in place.

The operation of the bracket according to the invention is generally illustrated in FIGS. 8a, 8b, 8c and 8d, wherein the bracket of the invention would be mounted on a maxillary right canine tooth being retracted distally toward the posterior tooth or teeth. A modified archwire receiving member, generally indicated by the numeral 16B, is shown in these figures. It will be understood this archwire receiving member will be rotationally mounted on a base (not shown) of the type similar to the base 15 of the first embodiment and which is suitably secured such as by bonding to the crown 90 of the tooth 91. It will also be understood that the archwire receiving member and the base will have bearing surfaces like those on the bearing bars of the first embodiment and that the archwire receiving member will be rotatably mounted on the base in a similar manner.

The modified archwire receiving member 16B includes a single tie wing having upper/gingival and lower/occlusal tie wing tips 94 and 95 over which an elastic ligature 98 can be mounted to retain an archwire 100 in the archwire slot of the archwire receiving member 16B. FIG. 8a illustrates the initial position of the tooth 91 and the relationship of the archwire to the tooth as well as the relationship of the archwire receiving member 16B to the tooth and the base (which is not shown). At this time, the archwire receiving member is not locked to the base and is free to rotate on the base.

Thereafter, employing retraction mechanics which includes application of forces to the tooth 91 to cause it to tip and slide along the archwire, as shown in FIG. 8b, understanding the archwire is generally passive and the archwire receiving member is connected to the archwire, the archwire receiving member will essentially rotate in a counterclockwise direction, as indicated by the arrows 103. It will be appreciated that the bracket of this embodiment will allow free tipping of the tooth throughout the entire range of normal tooth movement during retraction mechanics without any mechanical interferences.

The rotation of the archwire receiving member on the base can only be prevented by the insertion of the removable locking pin. Following the tipping and sliding step of the tooth as in FIG. 8b, the archwire would be removed from the archwire receiving member after removing the elastic ligature and thereafter the archwire receiving member would be aligned with the base and locked in place by the locking pin 18B. As seen in FIG. 8c, the archwire would then be placed into the archwire slot and the archwire would be ligated to the bracket with the elastic ligature 98. The necessary flexing of the archwire 100, as generally shown in FIG. 8c would apply an uprighting force to rotate the tooth in the direction of the arrows 104. Thus, during this step the bracket receiving member is rotated to its original position, as shown in FIG. 8d.

Accordingly, when the archwire is reinserted, as seen in FIG. 8c, and ligated to the archwire receiving member, the forces applied by the archwire desiring to straighten the tooth will cause the tooth to be uprighted in the direction of arrows 104 to the position shown in FIG. 8*d*. It will be appreciated that other uprighting forces may be applied such as by an uprighting spring or a suitable force module in order to upright the tooth.

Figure 11:
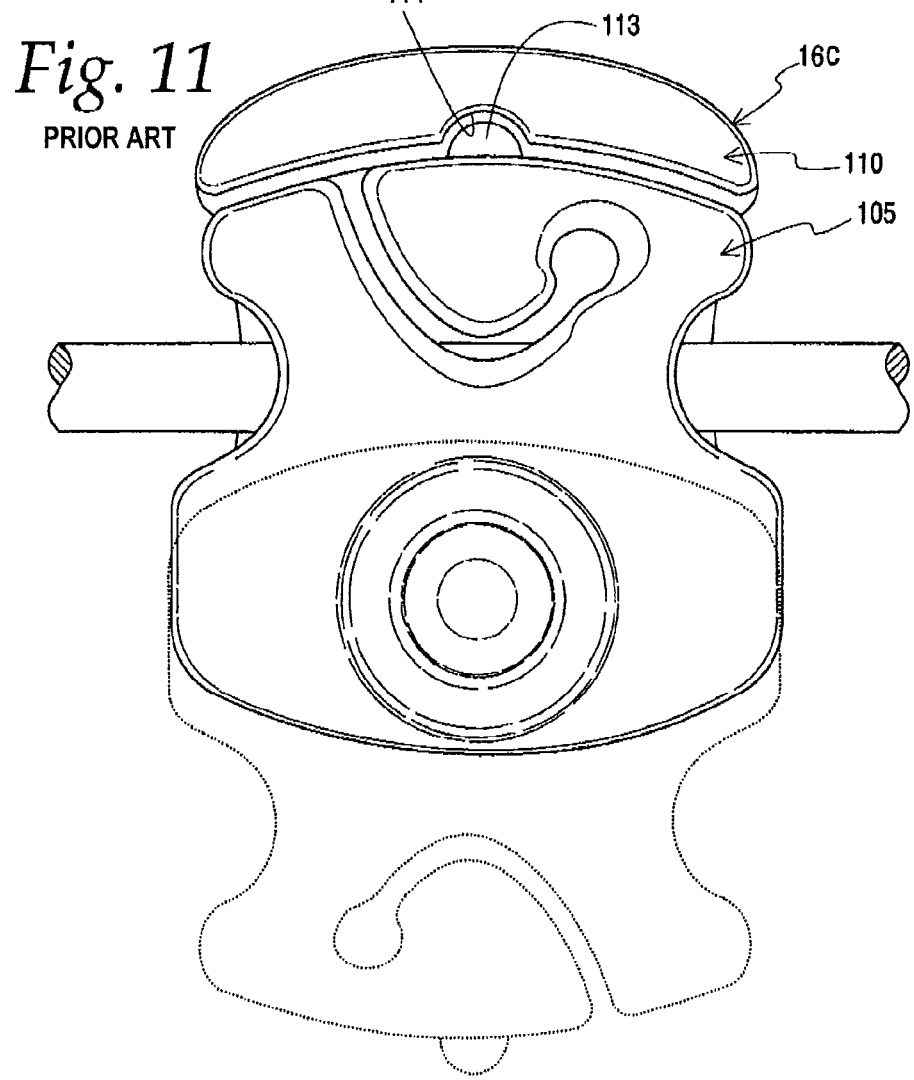
FIG. 11 is a front elevational view of a further modified locking pin.

As previously mentioned, it will be appreciated that any suitable archwire receiving member may be rotatably mounted on the base of the bracket. For illustrative purposes, a self-ligating archwire receiving member 16C is shown in FIG. 11. No claim is made to this specific self-ligating archwire receiving member, and it is known the illustrated member is already on the market. This member includes a rotatable closure or gate 105 coacting with an archwire receiving element 110. It will be appreciated that the closure 105 or gate can be swung to an open position, as shown in dotted lines, or in a closed position, as shown in solid lines. In the open position the archwire may be withdrawn or reinserted, and in the closed position the archwire is retained by the bracket. A locking detent 113 engages a locking indent 114 when in the closed and locked position.

While the invention has been described with respect to certain preferred embodiments, as will be appreciated by those skilled in the art, it is to be understood that the invention is capable of numerous changes, modifications and rearrangements and such changes, modifications and rearrangements are intended to be covered by the following claims.

The invention claimed is:

1. An orthodontic bracket mountable on a tooth coacting with an archwire for obtaining corrective movement to the tooth,
    said bracket comprising,
    a base and an archwire receiving member,
    said bracket base mountable on a tooth,
    said archwire receiving member having a rectangularly shaped outwardly facing archwire slot coacting with said base to produce a predetermined prescription and for receiving an archwire sized to allow sliding of the bracket along said archwire,
    means for rotatably mounting said archwire receiving member on said base including a bearing in said archwire receiving member and a stub shaft extending from the base coacting with said bearing,
    means on the stub shaft coacting with means on said bearing to minimize friction between the base and archwire receiving member during rotation of the archwire receiving member,
    coacting bearing bars on said base and archwire receiving member having means to minimize friction therebetween, and
    means for selectively locking the archwire receiving member to the base at a predetermined position in final stages of treatment such that the archwire in said slot will apply forces to the bracket to move the tooth to the predetermined prescription.

2. The bracket of claim 1, wherein said bearing in said archwire receiving member is aligned with said archwire slot and extending substantially perpendicular to said slot.

3. The bracket of claim 2, wherein said means on said stub shaft coacting with said means on the bearing to minimize friction between the base and archwire receiving member includes a conical surface on said stud coacting with an opposing conical surface on said bearing, and protrusions on one of the conical surfaces engaging the other of said conical surfaces to reduce the friction therebetween so that said archwire receiving member freely rotates before the locking means is engaged.

4. The bracket of claim 1, wherein said means on said coacting bearing bars to minimize friction include protrusions on one of said bars engaging the other of said bars.

5. The bracket of claim 1, wherein said locking means includes a pin having spaced apart bars on said base and archwire receiving member and a pin insertable between said base and member when said bars are aligned to engage said bars and prevent rotation of said member on said base.

6. The bracket of claim 5, wherein said pin is U-shaped and includes spaced apart legs extending from a connecting bar, and said legs engage said bars to lock the archwire receiving member in a predetermined position on said base.

7. The bracket of claim 5, wherein said pin includes means for self-locking the pin in place upon insertion between the base and archwire receiving member and against said bars.

8. The bracket of claim 7, wherein said pin includes means for facilitating removal of the pin.

9. The bracket of claim 5, wherein said pin includes means coacting with said bars to seat the pin in a predetermined locking position.

10. The bracket of claim 1, wherein said archwire receiving member includes a pair of opposed wing tips for receiving a ligature to retain the archwire in said slot.

11. The bracket of claim 1, wherein said archwire receiving member includes a slot closure member rotatable on said archwire receiving member selectively movable to open and close the slot for retaining the archwire in the slot.

12. An orthodontic bracket mountable on a tooth coacting with an archwire for obtaining corrective movement to the tooth,
    said bracket comprising,
    a base and an archwire receiving member,
    said bracket base mountable on a tooth,
    said archwire receiving member having a rectangularly shaped outwardly facing archwire slot coacting with said base to produce a predetermined prescription and for receiving an archwire sized to allow sliding of the bracket along said archwire,
    means for rotatably mounting said archwire receiving member on said base including a bearing in said archwire receiving member and a stub shaft extending from the base coacting with said bearing, and
    means for selectively locking the archwire receiving member to the base at a predetermined position in final stages of treatment such that the archwire in said slot will apply forces to the bracket to move the tooth to the predetermined prescription.

13. The bracket of claim 12, wherein said bearing in said archwire receiving member is aligned with said archwire slot and extending substantially perpendicular to said slot.

14. The bracket of claim 12, wherein said locking means includes spaced apart bars on said base and archwire receiving member and a pin insertable between said base and member when said bars are aligned to engage said bars and prevent rotation of said member on said base.

15. The bracket of claim 14, wherein said pin is U-shaped and includes spaced apart legs extending from a connecting bar, and said legs engage said bars to lock the archwire receiving member in a predetermined position on said base.

16. The bracket of claim 14, wherein said pin includes means for self-locking the pin in place upon insertion between the base and archwire receiving member and against said bars.

17. The bracket of claim 14, wherein said pin includes means coacting with said bars to seat the pin in a predetermined locking position.

18. The bracket of claim 12, wherein said archwire receiving member includes a pair of opposed wing tips for receiving a ligature to retain the archwire in said slot.

19. The bracket of claim 12, wherein said archwire receiving member includes a slot closure member rotatable on said archwire receiving member selectively movable to open and close the slot for retaining the archwire in the slot.

* * * * *